United States Patent
Fontaine et al.

(10) Patent No.: US 8,021,613 B2
(45) Date of Patent: Sep. 20, 2011

(54) SYSTEM AND METHOD FOR SELF-REFERENCING A SENSOR IN A MICRON-SIZED DEEP FLOW CHAMBER

(75) Inventors: Norman H. Fontaine, Painted Post, NY (US); Prantik Mazumder, Ithaca, NY (US); Mark A. Quesada, Horseheads, NY (US); Eric J. Mozdy, Elmira, NY (US); Po Ki Yuen, Corning, NY (US)

(73) Assignee: Corning Incorporated, Corning, NY (US)

( * ) Notice: Subject to any disclaimer, the term of this patent is extended or adjusted under 35 U.S.C. 154(b) by 1043 days.

(21) Appl. No.: 11/900,263

(22) Filed: Sep. 11, 2007

(65) Prior Publication Data

US 2008/0063569 A1 Mar. 13, 2008

Related U.S. Application Data

(62) Division of application No. 10/993,565, filed on Nov. 18, 2004, now Pat. No. 7,285,420.

(51) Int. Cl.
*G01N 15/06* (2006.01)
*G01N 21/00* (2006.01)
*G01N 21/76* (2006.01)

(52) U.S. Cl. .............. 422/68.1; 422/82.05; 422/82.11; 436/164; 436/172; 356/73

(58) Field of Classification Search ................ None
See application file for complete search history.

(56) References Cited

U.S. PATENT DOCUMENTS

| | | | |
|---|---|---|---|
| 4,642,469 A * | 2/1987 | Bretaudeau et al. ..... 250/559.31 |
| 4,815,843 A | 3/1989 | Tiefenthaler et al. ......... 356/128 |
| 5,313,264 A | 5/1994 | Ivarsson et al. ................. 356/73 |
| 5,716,852 A | 2/1998 | Yager et al. ..................... 436/172 |
| 5,869,004 A | 2/1999 | Parce et al. ..................... 422/100 |
| 5,972,710 A | 10/1999 | Weigl et al. ..................... 436/34 |
| 6,103,479 A | 8/2000 | Taylor ............................. 435/7.2 |
| 6,200,814 B1 | 3/2001 | Malmqvist et al. ............ 436/52 |
| 6,555,389 B1 | 4/2003 | Ullman et al. ................. 436/514 |
| 6,570,657 B1 | 5/2003 | Hoppe et al. |
| 6,627,406 B1 | 9/2003 | Singh et al. .................... 435/7.1 |
| 7,057,720 B2 | 6/2006 | Caracci et al. ................. 356/300 |
| 2002/0113095 A1 | 8/2002 | Jeon et al. .................. 222/424.5 |
| 2002/0127565 A1 | 9/2002 | Cunningham et al. ............ 435/6 |
| 2002/0168295 A1 | 11/2002 | Cunningham et al. ..... 422/82.05 |
| 2003/0017580 A1 | 1/2003 | Cunningham et al. ..... 435/287.2 |

(Continued)

FOREIGN PATENT DOCUMENTS
EP    0 202 021    11/1986

(Continued)

OTHER PUBLICATIONS

James P. Brody et al., "Biotechnology at Low Reynolds Numbers", Biophysical Journal, vol. 71, Dec. 1996, pp. 3430-3441.

(Continued)

*Primary Examiner* — Jill Warden
*Assistant Examiner* — Neil N Turk
(74) *Attorney, Agent, or Firm* — Gregory B. Butler; Thomas R. Beall

(57) ABSTRACT

A system and method are described herein for self-referencing a sensor that is used to detect a biomolecular binding event and/or kinetics which occur in a sample solution flowing along side a reference solution in a micron-sized deep flow channel.

14 Claims, 11 Drawing Sheets

U.S. PATENT DOCUMENTS

| | | | |
|---|---|---|---|
| 2003/0017581 A1 | 1/2003 | Li et al. .................. 435/287.2 |
| 2003/0022388 A1 | 1/2003 | Roos et al. ................ 436/164 |
| 2003/0026891 A1 | 2/2003 | Qiu et al. ..................... 427/58 |
| 2003/0027327 A1 | 2/2003 | Cunningham et al. ..... 435/287.2 |
| 2003/0027328 A1 | 2/2003 | Cunningham et al. ..... 435/287.2 |
| 2003/0032039 A1 | 2/2003 | Cunningham et al. ............ 435/6 |
| 2003/0059855 A1 | 3/2003 | Cunningham et al. ......... 435/7.9 |
| 2003/0068657 A1 | 4/2003 | Lin et al. ..................... 435/7.9 |
| 2003/0077660 A1 | 4/2003 | Pien et al. ..................... 435/7.1 |
| 2003/0092075 A1 | 5/2003 | Pepper ........................ 435/7.9 |
| 2003/0113766 A1 | 6/2003 | Pepper et al. ..................... 435/6 |
| 2004/0132172 A1 | 7/2004 | Cunningham et al. ..... 435/287.2 |
| 2004/0132214 A1 | 7/2004 | Lin et al. ..................... 436/518 |
| 2004/0151626 A1 | 8/2004 | Cunningham et al. .......... 422/58 |
| 2004/0223881 A1 | 11/2004 | Cunningham et al. ..... 422/82.05 |
| 2005/0099622 A1 | 5/2005 | Caracci et al. ................ 356/300 |
| 2005/0236554 A1 | 10/2005 | Fontaine et al. ............ 250/208.1 |
| 2006/0141527 A1 | 6/2006 | Caracci et al. ................ 435/7.1 |

FOREIGN PATENT DOCUMENTS

| | | |
|---|---|---|
| EP | 1 021 703 | 11/2001 |
| JP | 7-159319 | 1/1997 |
| JP | 2001-330560 | 5/2003 |
| WO | WO 99/05512 | 2/1999 |
| WO | WO 02/081085 | 10/2002 |

OTHER PUBLICATIONS

Stephan K.W. Dertinger et al., "Generation of Gradients Having Complex Shapes Using Microfluidic Networks", Anal. Chem., 2001, vol. 73, pp. 1240-1246.

Biacore S51, Product Information Brochure, Mar. 14, 2003, www.biacore.com.

* cited by examiner

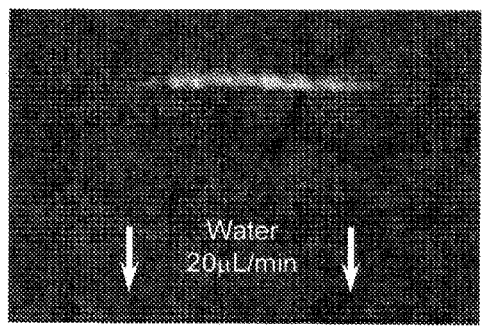 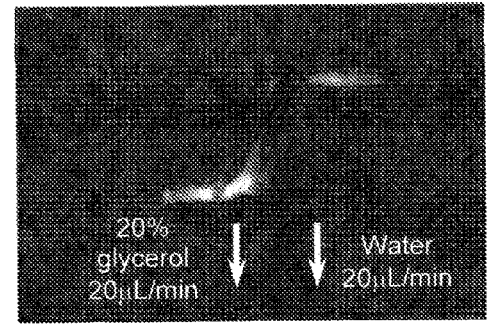
FIG. 5A  FIG. 5B
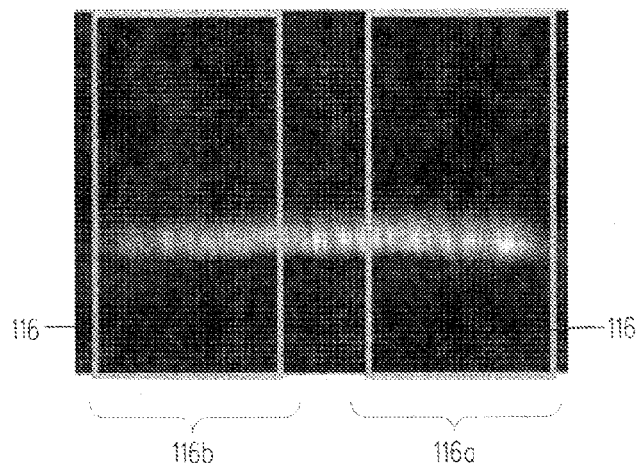
FIG. 6A

SYSTEM AND METHOD FOR SELF-REFERENCING A SENSOR IN A MICRON-SIZED DEEP FLOW CHAMBER

This is a divisional of application Ser. No. 10/993,565, filed Nov. 18, 2004, now U.S. Pat. No. 7,285,420, entitled "SYSTEM AND METHOD FOR SELF-REFERENCING A SENSOR IN A MICRON-SIZED DEEP FLOW CHAMBER".

BACKGROUND OF THE INVENTION

1. Field of the Invention

The present invention relates in general to a system and method for self-referencing a sensor that is used to detect if a biomolecular binding event occurred in a sample solution flowing along side a reference solution in a micron-sized deep flow channel. In one embodiment, the sensor and micron-sized deep flow channel are incorporated within a well of a microplate.

2. Description of Related Art

The performance of sensors based on optical detection techniques such as surface plasmon resonance (SPR), waveguide grating-based surface sensing, and surface or bulk scattering is generally affected by the designs and characteristics of the sensors, the optics, and by the environmental fluctuations. Unwanted sensitivity to environmental fluctuations including temperature change, mechanical vibration, and source drift (among others) is the most common problem affecting the performance of the sensors. Existing instrument's like the Biacore® S51 which is made and sold by Biacore AB in Uppsala, Sweden are equipped with temperature control features which help minimize the effect of temperature fluctuations on the performance of the sensor. However, these types of instruments are expensive, and temperature control alone cannot correct for all environmental factors.

Other instruments attempt to diminish the impact of environmental fluctuations by providing a self-referencing method and/or a common environment for the reference and detection regions such that any environmental fluctuations can be referenced out. Three such instruments have been described in U.S. Pat. No. 6,200,814 B1 and EP1021703 B1 (Malmqvist et al.) and U.S. Pub. No. US2003/0022388 A1 (Roos et al.). Malmqvist et al. disclose methods and devices for controlling the fluid flow over a sensing surface within a flow cell such that selective sensitization of discrete sensing areas is permitted and selective contact of the discrete sensing areas with a sample fluid flow is provided. And, Roos et al. discloses a method for adjusting the position of the interface between fluids in the longitudinal direction of the flow cell by controlling the relative flow rates of the fluids.

One shortcoming of these instruments is that their surface sensors do not cover the whole width of the flow cell and as a result more than one surface sensor is required to cover the whole width of the flow cell in certain embodiments. Thus, in order to reference out any environmental fluctuations or non-specific biomolecular binding, at least two surface sensors are required in the flow cell, one for the referencing and one for the detection. By using more than one spatially separated sensor, the optics required for the detection are increased by the number of sensors added. As a result, there may be a physical limitation of how close the sensors can be positioned together and the number of sensors that can be used in the flow cell. Also, the different sensors may experience different environmental fluctuations and may have different characteristics and performances. All of these differences add to the uncertainty and hence can adversely affect the accuracy of detecting a biomolecular binding event.

Another shortcoming of these instruments is that they rely on a dynamic interface between the multiple laminar flows and then use the movement of the fluid interface as a key component of their referencing methodology. While both sample and reference fluids are present in the flow cell, the interface between the two fluids is adjusted to place the sample fluid stream exclusively over the sensor, then the fluid interface is further modified (via flow rate, etc.) so as to place the reference fluid over the same sensing region, thereby presenting a reference signal. While this method efficiently utilizes a single sensing region for both sample and reference fluids, the movement of the fluid interface can cause a disruption of the laminar flows, promote mixing of the streams, and thereby degrade the signals. Furthermore, accurate movement of the fluid interface requires impeccable control over the dimensions of the fluidic channel, fluid flow rates, etc. In addition, due to the movement of the fluid interface, the sample and reference signals are not measured at the same time which will decrease the accuracy of the self-referencing method.

Accordingly, there is a need for a system and method for self-referencing a sensor that addresses the aforementioned shortcomings and other shortcomings of the traditional instruments. This need and other needs are satisfied by the system and method of the present invention.

BRIEF DESCRIPTION OF THE INVENTION

The present invention includes a system and method for self-referencing a sensor that is used to detect a biomolecular binding event which occurred in a sample solution flowing along side a reference solution in a micron-sized deep flow channel. In one embodiment, the system includes an interrogation system that directs an input optical beam at the sensor which has a sensing region within the sample solution and the reference solution that flow side-by-side to one another in the micron-sized deep flow channel. The interrogation system receives an output optical beam from the sensor. The system also includes a computer or other electrical hardware to analyze the output optical beam, to determine a detection signal associated with the sample solution flowing in a detection region of the sensing region of the sensor and to determine a reference signal associated with the reference solution flowing in a reference region of the sensing region of the sensor. The computer (or equivalent electrical circuit) then subtracts the reference signal from the detection signal so as to generate a corrected detection signal which indicates whether or not a biomolecular binding event occurred in the sample solution flowing in the micron-sized deep flow channel. In this way, the system is able to self-reference the sensor and mitigate the uncertainties in the detection signal that are due to environmental conditions.

BRIEF DESCRIPTION OF THE DRAWINGS

A more complete understanding of the present invention may be had by reference to the following detailed description when taken in conjunction with the accompanying drawings wherein:

FIGS. 5A and 5B are two time-lapsed photographs showing shifts in resonance images measured by the system shown in FIG. 4;

FIGS. 6A and 6B are two diagrams that respectively illustrate an image of a response from the sensor and an image of two separate angular resonance plots obtained from the response image during an experiment performed to demonstrate the capabilities of the system shown in FIG. 4;

DETAILED DESCRIPTION OF THE DRAWINGS

Figure 1:
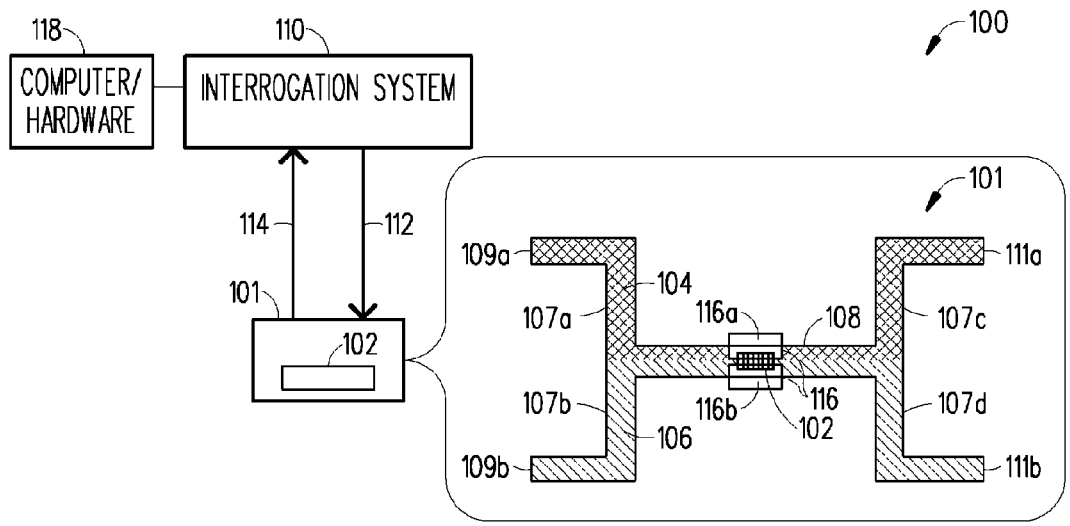
FIG. 1 is a block diagram illustrating the basic components of a system in accordance with the present invention.
Figure 2:
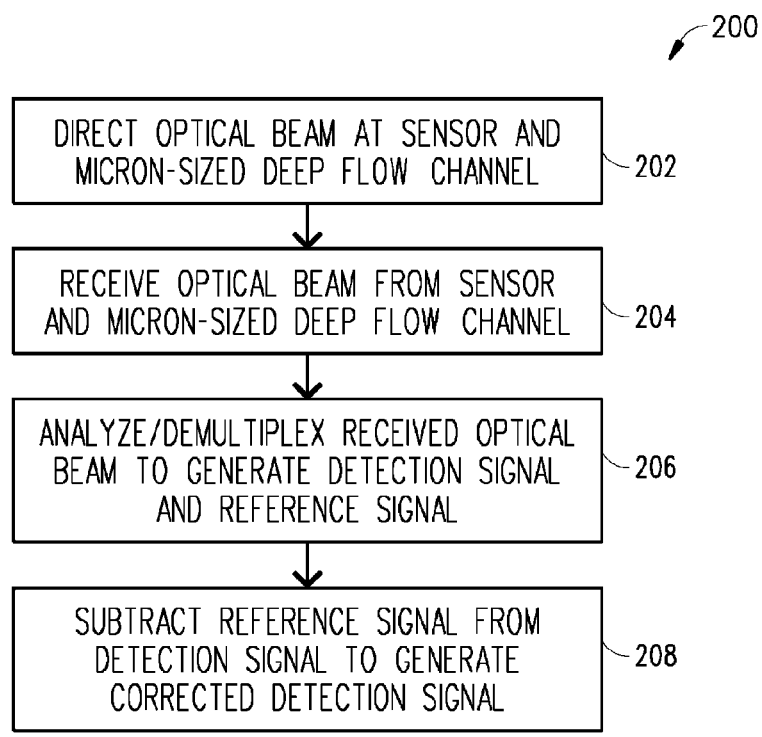
FIG. 2 is a flowchart illustrating the basic steps of a preferred method for self-referencing a sensor located in a microfluidic device of the system shown in FIG. 1 in accordance with the present invention.
Figure 3A:
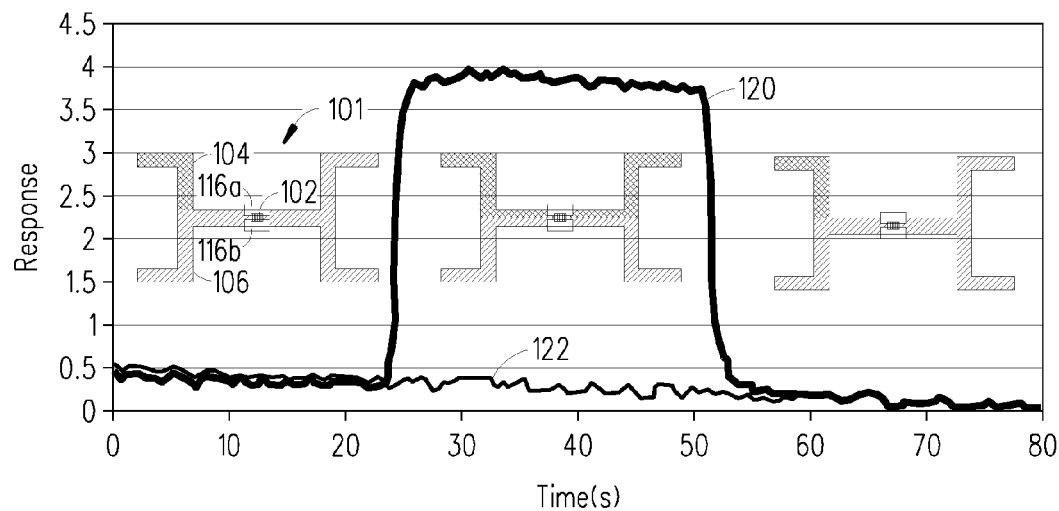
FIGS. 3A-3B are two diagrams illustrating in greater detail the structure of the microfluidic device and sensor shown in FIG. 1.
Figure 3B:
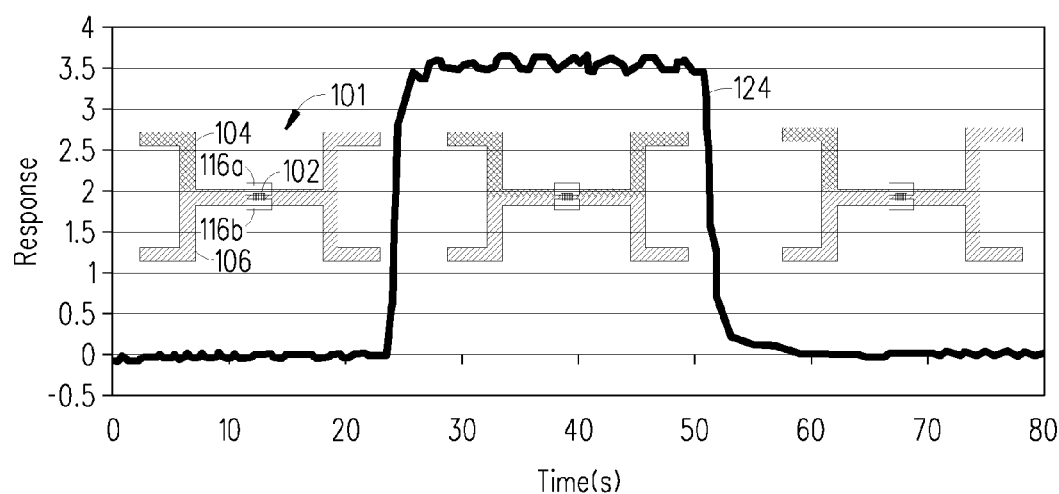

Referring to FIGS. 1-3, there are shown several diagrams of the preferred embodiment of a system 100 and method 200 for self-referencing a sensor 102 (e.g., grating-coupled waveguide sensor 102, surface plasmon resonance sensor 102) located within or below a microfluidic device 101. The sensor 102 is used to detect whether or not a biomolecular binding event occurred in a sample solution 104 that is flowing next to a reference solution 106 in a micron-sized deep flow channel 108 of the microfluidic device 101. In particular, the sensor 102 is located within or below the micron-sized deep flow channel 108 in which the sample solution 104 and the reference solution 106 flow side-by-side to one another over a sensing region 116 of the sensor 102 (see expanded view in FIG. 1). As can be seen in the expanded view in FIG. 1, the exemplary microfluidic device 101 has multiple flow channels 107a, 107b, 107c and 107d that share the common micron-sized deep flow channel 108 which is superimposed on the sensing region 116 of the sensor 102. The microfluidic device 101 also has two inlets 109a and 109b and two outlets 111a and 111b (only one outlet 111a or 111b in the microfluidic device 101 is also possible). As shown, the two fluids 104 and 106 can be flowed simultaneously into the flow channel 108 by opening the two inlets 109a and 109b. Also, at any given time, one of the inlets 109a or 109b can be closed such that only one fluid 104 or 106 can flow through the common flow channel 108.

The system 100 includes an interrogation system 110 that directs (step 202) an optical beam 112 at the sensor 102 and receives (step 204) an optical beam 114 from the sensor 102. The system 100 further includes a computer/processor (or equivalent electrical hardware) 118 that analyzes/demultiplexes (step 206) information associated with the optical beam 114 and generates a detection signal 120 which is associated with the sample solution 104 that is flowing in a detection region 116a of the sensing region 116 of the sensor 102 (see FIG. 3A). The computer (or electrical hardware) 118 also analyzes/demultiplexes (step 206) information associated with the optical beam 114 and generates a reference signal 122 which is associated with the reference solution 106 that is flowing in a reference region 116b of the sensing region 116 of the sensor 102 (see FIG. 3A). The computer (or equivalent electrical circuit) 118 then subtracts (step 208) the reference signal 122 from the detection signal 120 and generates a corrected detection signal 124 (see FIG. 3B). The corrected detection signal 124 effectively indicates whether or not a biomolecular binding event occurred in the sample solution 104 while mitigating unwanted environmental effects.

The system 100 and method 200 are a marked improvement over the prior art in that only one sensor 102 is required for both simultaneous detection and referencing, which reduces the complexity of the optics, the instruments, and the number of sensors required. As described above, in the present invention the reference signal 122 is generated from the same sensor 102 that is used for the detection. Furthermore, unlike the prior art, the fluidic interface between detection and reference fluids 104 and 106 may be kept constant, preventing turbulent mixing, hysteresis, and repeatability problems inherent in moving fluidic interface systems. In addition, since both sample and reference signals are measured at the same time, any sudden short environmental fluctuations can be referenced out making the self-referencing method 200 more accurate and robust. And, since the sample solution 104 and the reference solution 106 flow next to one another in the micron-sized deep flow channel 108 they both experience the same environmental fluctuations as do the reference signal 122 and the detection signal 120. It is this fact that enables the system 100 to mitigate the undesirable environmental effects by subtracting the reference signal 122 from the detection signal 120 to generate the corrected detection signal 124.

This is all possible since, when two streams of fluids 104 and 106 flow side by side in a micron-sized deep channel 108, the only means of mixing the two fluids 104 and 106 is by molecular diffusion. The small length scale and height of the channel 108 preclude any possibility of eddy diffusivity due to turbulence and/or shear layer instability between the two fluids 104 and 106. In this micron high fluid channel mass diffusivity of the molecular entities of the two fluids 104 and 106 typically employed for drug discovery investigations is many orders of magnitude smaller that the thermal diffusivity of the two fluids 104 and 106. This leads to disparate thermal and mass diffusion length scales in the channel 108. Due to smallness of the mass diffusivity, the two streams 104 and 106 are well separated by a very thin diffusion layer, which grows relative to the amount of time the two fluids 104 and 106 are in contact. The magnitude of the diffusion interface can be obtained by using the equation $\sqrt{2Dt}$ where D is the mass diffusion coefficient and t is time (t=L/U, where L is the distance of the sensing region from the inlet, and U is the average flow velocity). The small value of D (e.g., D for the small molecule fluorescein biotin and the protein bovine serum albumin are $3.4\times10^{-6}$ cm$^2$s$^{-1}$ and $6.5\times10^{-7}$ cm$^2$s$^{-1}$, respectively) ensures that the chemical/compositional integrity of each stream 104 and 106 is maintained except in a very thin layer near the center. On the other hand, the large value of thermal diffusivity ensures that the lateral temperature distribution in the channel 108 is uniform since the thermal boundary layer grows as $\sqrt{2\alpha t}$, where $\alpha$ is the thermal diffusivity (e.g., $\alpha=1.4\times10^{-3}$ cm$^2$s$^{-1}$ for water). By exploiting the disparate mixing length scales of heat and mass, the self-referencing system 100 and method 200 is able to use one sensor 102 to investigate interactions between biomolecules in the sensing area 116. This type of self-referencing effectively reduces or removes the sensitivity that the sensor 102 has to perturbations in angle, location, temperature, source wavelength, thermal expansion of instrumentation, and even some non-specific binding between biomolecules in the sample solution 104.

Figure 6B:
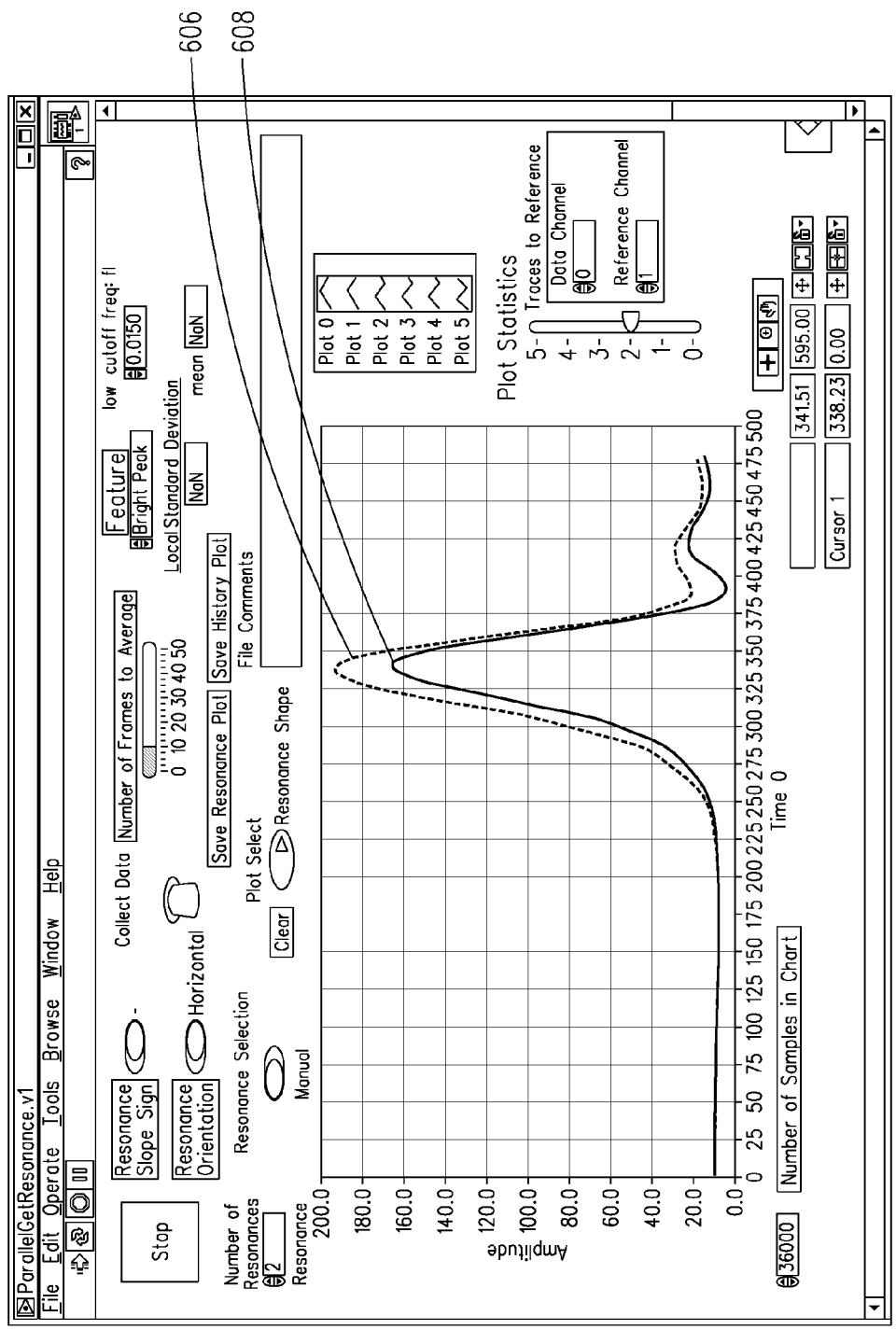

The interrogation system 110 typically used to interrogate the sensor 102 utilizes an optical beam 112 that has the appropriate spectral or angular content, such that when the optical beam 112 is reflected by the sensing surface the angular or wavelength content is altered by the presence of the analyte 114. This includes the possibility for surface plasmon resonance use, in which the measured quantity is the absorption of a set of angles or wavelengths from the input beam and not a resonant reflection. The interrogation system 110 can take many forms, and two general embodiments are described herein. In one embodiment, the interrogation system 110 delivers a single-wavelength, high-angular content optical beam 112 to the sensor 102, and the output beam 114 retains some angular response information from the sensor 102. This type of interrogation system 110 is commonly referred to as an angular interrogation system 110a since angular detection is employed to locate a dominant angle in the output beam 114 (see FIGS. 4-6). Another embodiment of the interrogation system 110 involves delivering a collimated optical beam 112 containing a plurality (band) of wavelengths to the sensor 102, where the output beam 114 provides some information on the wavelength response of the sensor 102. This type of interrogation system 110 is commonly referred to as a spectral interrogation system 110b since the spectrum of the output beam 114 is analyzed to locate the resonance in wavelength space (see FIGS. 7-8).

The differences between the angular interrogation system 110a (FIG. 4) and the spectral interrogation system 110b (FIG. 7) are somewhat transparent because the relationship between angle and wavelength for many sensors of the evanescent-field type is linear. For this reason, the main difference between the two modalities is related to the extra step in the spectral detection of measuring the wavelength spectrum of the output beam. This means the detection systems for the two systems could be theoretically identical, except for a wavelength-discriminating element in front of the detector/camera.

Figure 7:
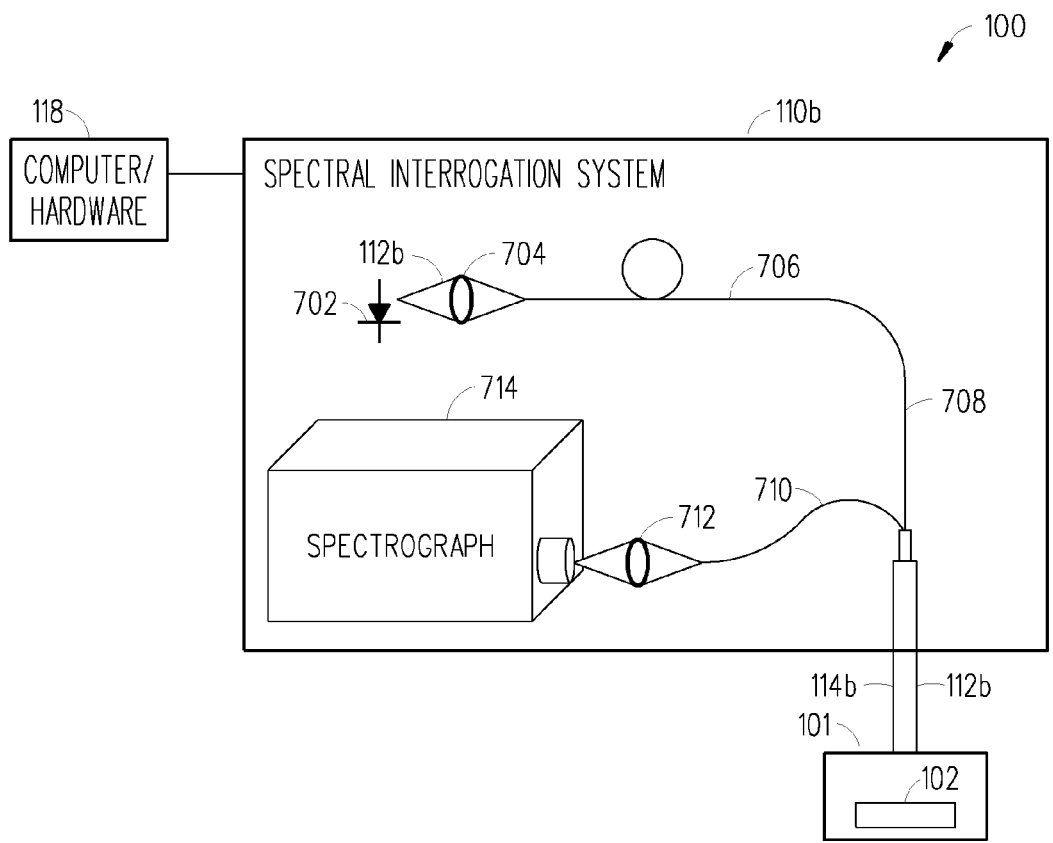
FIG. 7 is a block diagram illustrating a second embodiment of the system shown in FIG. 1 which utilizes a spectral interrogation system in accordance with the present invention.
Figure 8:
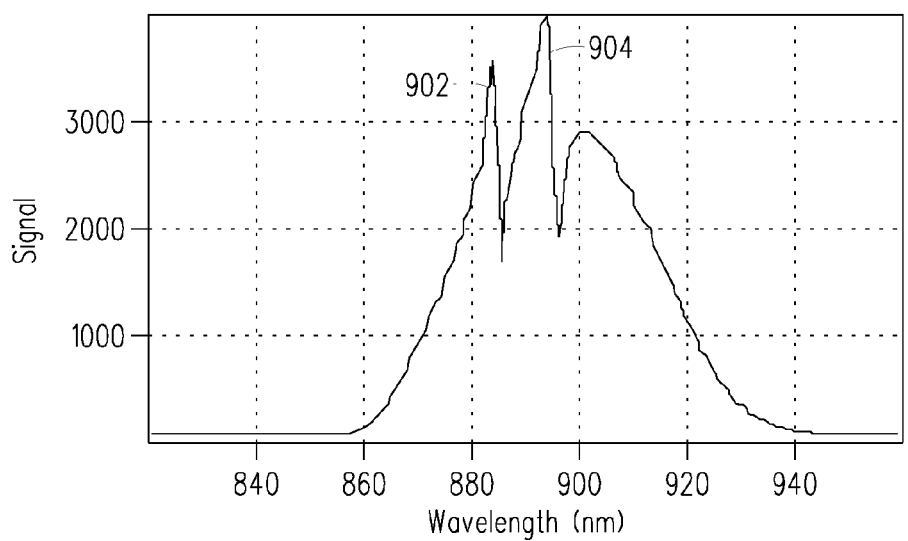
FIG. 8 is a graph that shows an example of multiple resonant responses in an output beam received by the spectral interrogation system shown in FIG. 7.

A larger difference in instrument systems is based upon the choice of optical delivery: the input/output light can be delivered to/from the sensor via free space (shown for example in the angular system of FIG. 4) or an optical waveguide (exemplified by the optical fiber in the spectral system of FIG. 7). It should be noted that either the angular or spectral embodiments can be implemented with either the free-space or waveguide-delivered approach, in many different combinations (input and output beams). The difference between free-space and waveguide-delivered input light becomes important with respect to the present invention because the computer 118 needs to analyze/demultiplex the received optical beam 114 in different ways to generate the corrected detection signal 124. In the free-space delivery associated with the angular interrogation system 110a, the output beam 114 along the response direction of the sensor 102 is the far-field response originating from the sensing region 116. By properly spanning or sampling across the width of the sensing region with the input beam 112, and by imaging each sensing regions' response onto a detector, the output response profile 114 across the width of the sensor 102 can be resolved at the detection system and analyzed by the computer 118. In this manner, arbitrary flow zones above the sensor 102 may be measured simultaneously and separately from one another and then subsequently compared or referenced. In the case of the waveguide optical delivery of the spectral interrogation system 110b, the spatial information is typically lost during propagation within the fiber, so a different processing technique is required to demultiplex the optical beam 114 to distinguish between the different flow zones above the sensor 102. Both of these approaches are discussed in greater detail below with respect to FIGS. 4-8.

Figure 4:
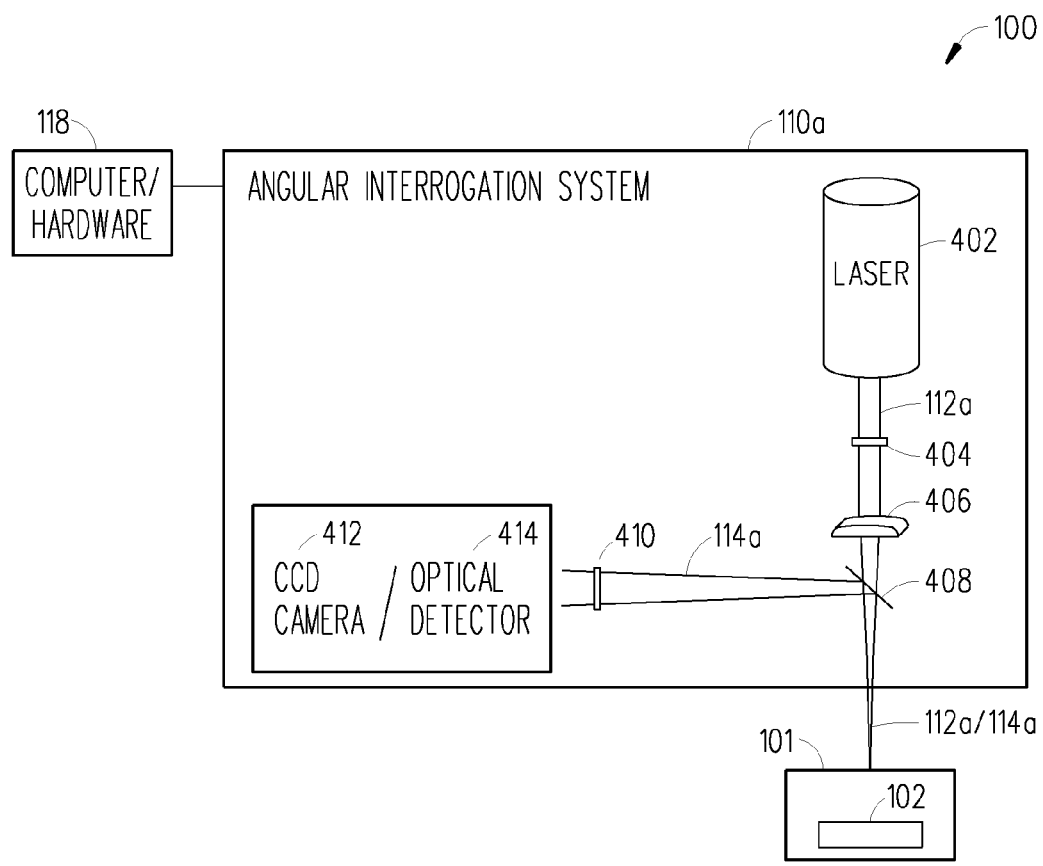
FIG. 4 is a block diagram illustrating a first embodiment of the system shown in FIG. 1 which utilizes an angular interrogation system in accordance with the present invention.

Referring to FIG. 4, there is a block diagram illustrating a first embodiment of the system 110a shown in FIG. 1 which utilizes an exemplary angular interrogation system 110a. The exemplary angular interrogation system 110a includes a laser 402 that emits the optical beam 112a which passes through a polarizer 404 (e.g., 45° polarizer 404), a cylindrical objective 406 (e.g., f~10 cm cylindrical objective 406) and a pick-off mirror or beamsplitter 408 before reaching the sensor 102 and microfluidic device 101. The illumination at the sensor 102 is made to be anamorphic (i.e. the incident beam 112a is focused along the sensors response direction and not focused in the perpendicular direction) such that the illumination forms a line which spans across the width of the sensor. The sensor 102 emits an optical response 114a across its width which is deflected by the pick-off mirror or beamsplitter 408 and passes through an analyzer (polarizer) 410 oriented at 90° to the polarizor 404 before reaching a CCD camera 412. Alternatively, an optical detector 414 (e.g. detector pair, one each for the detection and reference regions of the sensor 102) can replace the camera 412 as the detection element. The optical detector 414 may be more efficient and the data easier to analyze than the data from the CCD camera 412 because the optical detector 414 outputs a voltage which is indicative of the location of the resonance. In contrast, the CCD camera 412 outputs images that must be further analyzed to determine the measured response.

As shown, the laser/optical source 402 emits an optical beam 112a which has a collection of angles that interacts with the sensor 102. The sensor 102 responds by emitting an optical beam 114a to the CCD camera 412, which produces an image of the far-field response of the sensor region 116. The bright streak, for example, indicates the resonant response angles from across the width of the sensor 102 (see photographs in FIGS. 5A and 5B). In the photographs, the horizontal direction represents the extent of the response 112a reflected from across the width of the sensor 102, where this response width is limited by the spatial extent of the sensor 102. Hence, the vertical direction represents the angular response axis and the horizontal direction represents the location of the response that occurs across the width of the sensor. Movement of the bright strip in the vertical direction indicates a resonant response change, while differences in the image along the horizontal axis indicate different sensor region responses such as that expected when utilizing two different flows 104 and 106. It is this vertical resonant response change that is used to indicate whether or not there was a biomolecular binding event. It should be appreciated that for clarity the system 100 shown in FIG. 4 is illustrated as having only one optical beam that interfaces with one sensor 102. Of course, the system 100 can have the hardware (e.g., optics 404, 406, 410 and multiplexed optical detectors 414) that make it possible to emit and receive multiple optical beams to and from multiple sensors 102.

In an experiment to demonstrate the capabilities of the present invention, the inventors used an "H" shaped flow chamber with 4 mm width and 200 µm deep flow channel 108, a 3 mm×3 mm waveguide grating surface sensor 102 and an angular interrogation system 110*a* like the one shown in FIG. 4. This sensor 102 responded to index of refraction changes at the surface near a grating by changing the angular location or spectral maximum of a resonance response. The image of the response of the sensor 102 was divided by the computer 118 into two regions including a reference region 116*a* and a detection region 116*b* (see FIG. 6A). The computer 118 then analyzed the image to produce two separate angular resonance plots 606 and 608 (see FIG. 6B). One resonance plot 606 is associated with the detection half 116*a* of the flow channel 108, and the other resonance plot 608 is associated with the reference half 116*b* of the flow channel 108. The referencing was made possible by flowing a higher-index sample solution 104 (e.g., 0.5% glycerol) side-by-side with a lower-index buffer solution 106 (e.g., water) in one stream over the sensing region of the sensor 102 (see middle microfluidic device 101 in FIG. 3A). Since both solutions 104 and 106 flowed across the same sensor 102 without mixing, the single sensor 102 provided a response to each flow stream independently. As the sample solution 104 and the reference (buffer) solution 106 were flowed over the same sensor 102 with no physical separation between the fluid streams 102 and 104, the two sensing regions 116*a* and 116*b* of the sensor 102 exhibited a response to the sample fluid 104 and reference fluid 102, respectively (see detection signal 120 and reference signal 122 in FIG. 3A). Since the fluid streams 104 and 106 were in physical contact, the temperature and pressure of each flow was nearly identical, and since the data came from the same optical beam 114 and a single physical sensor 102, the angle, mechanical noise, laser noise, etc. were also nearly identical. The subtracted trace associated with the corrected detection signal 124 showed excellent flatness and response (see FIG. 3B).

Referring to FIG. 7, there is a block diagram illustrating a second embodiment of the system 110*b* shown in FIG. 1 which utilizes an exemplary spectral interrogation system 110*b*. The exemplary spectral interrogation system 110*b* includes a broadband light source 702 that emits the optical beam 112*b* which passes through a lens 704, an optical fiber 706 and a collimator 708 before reaching and interacting with the sensor 102 at a single angle. The sensor 102 emits optical beam 114*b* which is input into an optical fiber 710 (collection fiber 710) and passed through a lens 712 into a spectrograph 714. The optical beam 114*b* contains a spectral peak which corresponds to the resonance location.

As mentioned above, because the spatial information about the sensor 102 is lost during the waveguide propagation in the spectral interrogation system 110*b*, another means needs to be used to demultiplex the responses from the fluid flows 104 and 106 in the optical beam 114*b*. One solution is to duplicate the waveguide delivery/receive system 702, 704, 706, 708, 710 and 712 corresponding to the number of fluid flows 104 and 106 where in this example two fiber launch/receive systems 702, 704, 706, 708, 710 and 712 would be placed side-by-side under the two fluids 104 and 106 flowing above the sensor 102. This embodiment of course involves added complexity as well as cost, and the waveguide mechanics and optics need to physically fit and be precisely aligned under the sensor 102. Another solution could involve precisely moving or oscillating a single optical fiber launch/receive system 702, 704, 706, 708, 710 and 712 mechanically from one flow region 116*a* to the other flow region 116*b* when a measurement is desired from each flow 104 and 106. Yet another embodiment could be made feasible by appropriate differentiation of each sensor region 116*a* and 116*b*. For example, if the fluids 104 and 106 in the flow channel 108 are significantly different, or if different surface chemistries are applied via each separate flow, this may cause a large enough shift in each resonant signal relative to the other due to resultant waveguide differences so as to cause a spectral separation in the resonant responses. In other words, the need for spatial information is foregone by the large (necessarily unambiguous) spectral separation of the two flow regions 116*a* and 116*b*. This situation is shown schematically in the graph shown in FIG. 8, where two simultaneous peaks 902 and 904 are visible in a broadband source spectrum. These could correspond to the two different flow regions 116*a* and 116*b* and the tracking of each peak 902 and 904 represents the desired detection signal 120 and the reference signal 122. In either of these situations, the computer 118 subtracts the reference signal 122 from the detection signal 120 and generates the corrected detection signal 124. Again, the corrected detection signal 124 effectively indicates whether or not a biomolecular binding event occurred in the sample solution 104 while mitigating unwanted environmental effects.

Figure 9A:
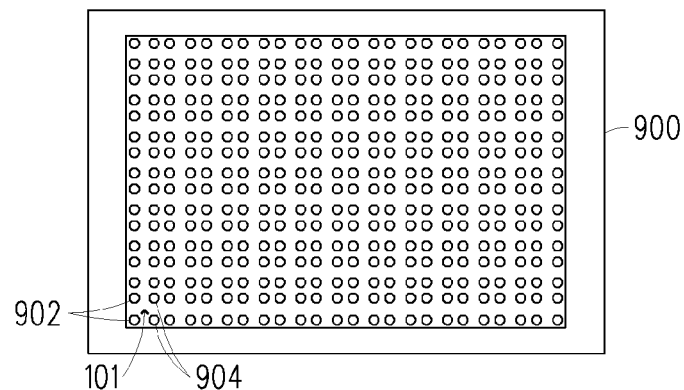
FIGS. 9A-9C respectively illustrate a top view, bottom view and cross-sectional side view of an exemplary 96-H well plate that incorporates multiple microfluidic devices and sensors that interface with the interrogation system and computer shown in FIG. 1.
Figure 9B:
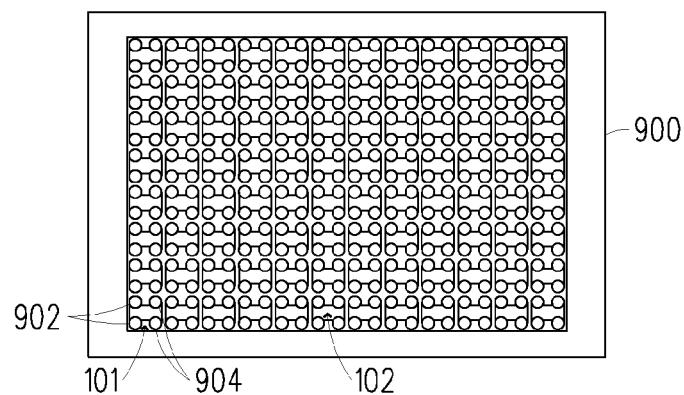
Figure 9C:
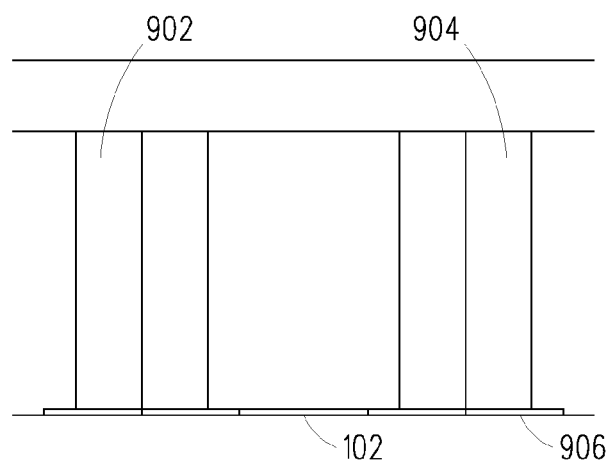

Referring to FIGS. 9A-9C, there are respectively illustrated a top view, bottom view and cross-sectional side view of an exemplary 96-H well plate 900 that incorporates multiple microfluidic devices 101 and sensors 102 that interface with the interrogation system 110 (not shown) and computer 118 (not shown). As can be seen from the top view of the 96-H well plate 900 shown in FIG. 9A, each "well" has four holes including two inlets 902 and two outlets 904. And, in the bottom view shown in FIG. 9B one can only see the "wells" in the shape of an H (the height of the H is a micron dimension) with four holes (two inlets 902 and two outlets 904) for each "well". Lastly, in the side view shown in FIG. 9C one can see an inlet 902, an outlet 904, sensor 102 and a micron-sized deep "H" shaped channel 906.

Figure 10A:
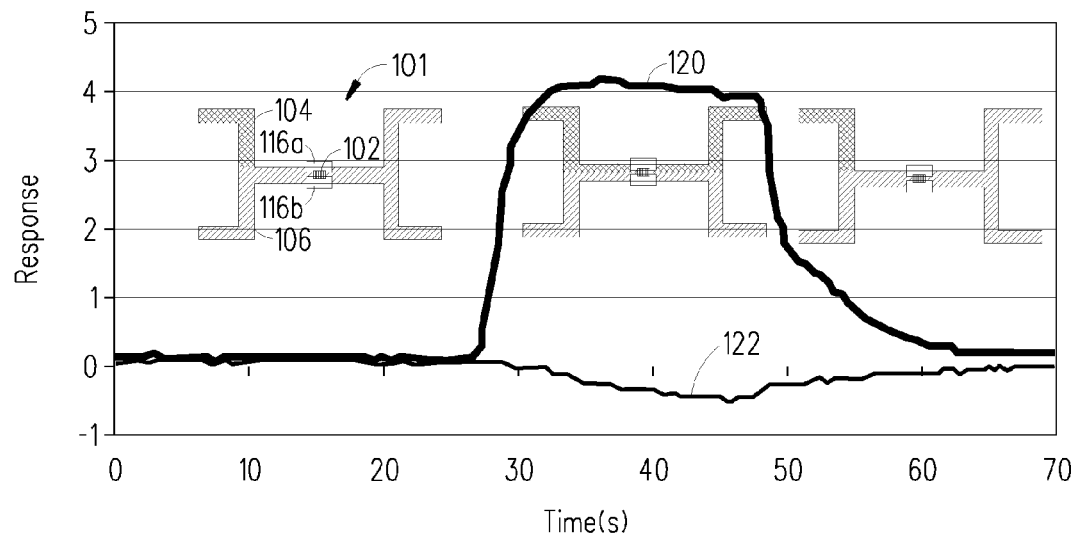
FIGS. 10A and 10B are two time plots illustrating the detection signal, the reference signal and the corrected detection signal that were obtained during an experiment performed to demonstrate the capabilities of the system shown in FIGS. 9A and 9B.
Figure 10B:
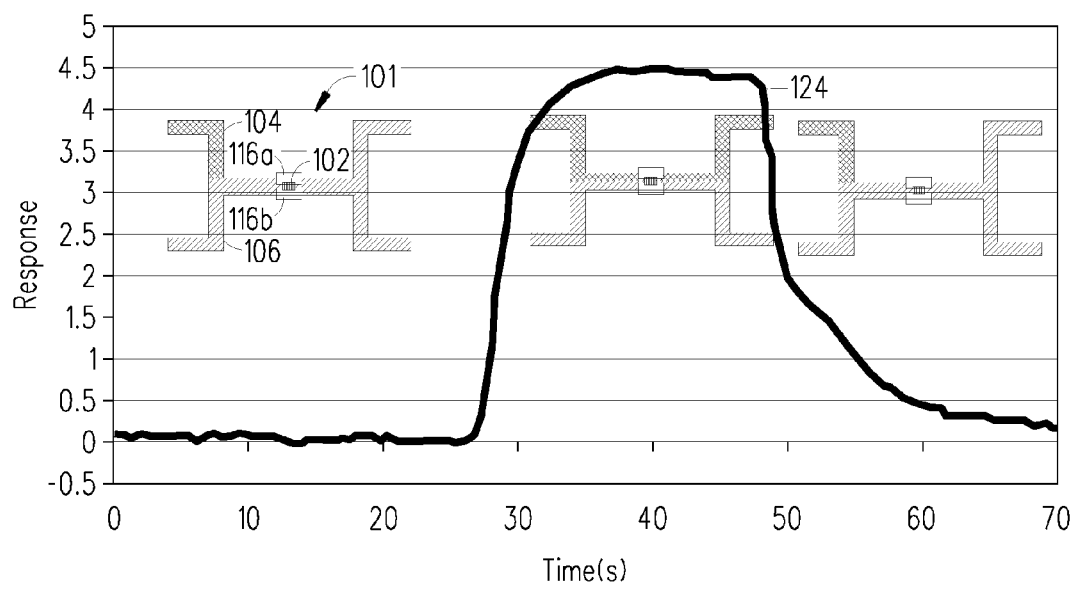

The interrogation system 110 when used to interrogate the 96-H well plate 900 is designed to emit an optical beam 112 at each sensor 102 in each device 101 and receive an optical beam 114 from each sensor 102 in each device 101. In this way, multiple sensors 102 can be interrogated at the same time. For instance, either a CCD camera 412 or multiplexed optical detector system 414 can receive the plurality of optical beams 114 from the sensor array 102. If the multiplexed detector system 414 is used the plurality of beams is demultiplexed by virtue of impinging upon separate detectors. As described previously, each optical detector (e.g. detector pair, one for each of the detection and reference regions of a sensor) can then demultiplex the detection signal 120 and reference signal 122 from the different regions of an individual sensor. If the CCD camera 412 is used then the computer/processor 118 analyzes/demultiplexes the plurality of optical beams 114 from the sensor array, and also analyzes/demultiplexes each optical beam 114 in order to generate detection signals 120 and reference signals 122 that are subtracted from one another to determine the corrected detection signals 124. Each corrected detection signal 124 effectively indicates whether or not a biomolecular binding event occurred in the sample solution 104 located in the corresponding device 101. FIGS. 10A and 10B are two time plots illustrating the detection signal 120, the reference signal 122 and the corrected detection signal 124 obtained during an experiment performed to demonstrate the capabilities of the system 100 and 96-H-well plate 900 shown in FIGS. 9A-9C. See also FIGS. 5A and 5B, where the two photographs which show the zoning of two fluids 104 and 106 were also obtained during the performance of this experiment.

Figure 11:
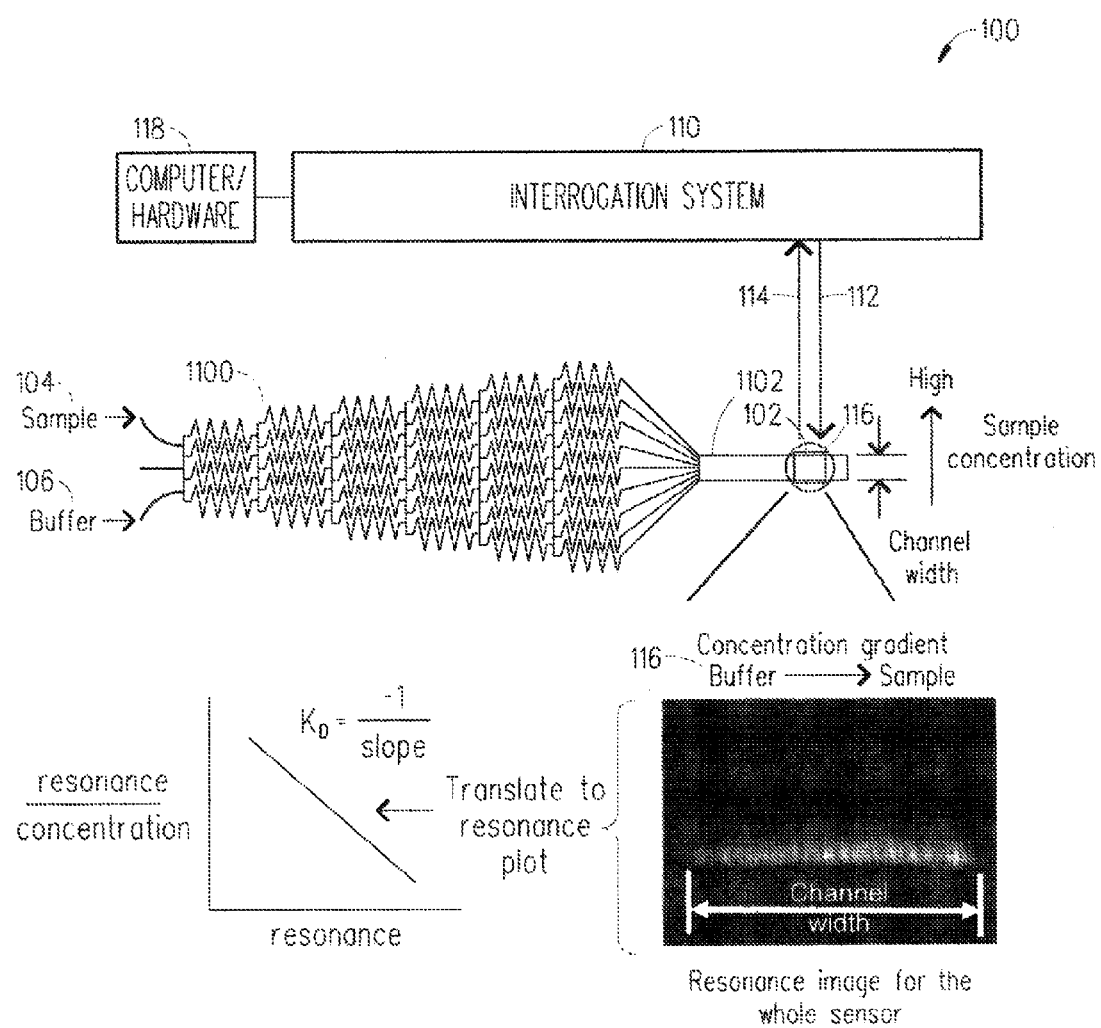
FIG. 11 illustrates several diagrams of a third embodiment of the system shown in FIG. 1 which analyzes a microfluidic device that is capable of generating multiple concentration gradients in a sample solution in accordance with the present invention.

Referring to FIG. 11, there are shown several diagrams associated with a third embodiment of a system 100. In this embodiment, the interrogation system 110 outputs the optical beam 112 to the sensor 102 and receives the optical response 114 from the sensor 102 which is then divided by the computer 118 into independent signals corresponding to each concentration of the sample fluid 104 and the reference fluid 106 in the flow chamber 1102. In particular, the microfluidic device 1100 generates multiple concentration gradients in the sample solution 104 which flows in a micron-sized deep flow chamber 1102 and the computer 118 analyzes the output optical beam 114 to determine multiple corrected detection signals 124 which correspond with the multiple concentration gradients in the sample solution 104. As shown, the micron-sized deep flow chamber 1102, with parallel flow channels, is made to be coincident with a sensing region 116 of the sensor 102. An advantage of this embodiment is that a single sensor 102 can be used to make parallel measurements for gradient analysis. And, another advantage of this embodiment is that by performing one experiment, different concentrations of the sample fluid 104 can be simultaneously generated and used for measurement. One could also use this arrangement to analyze a sample and determine an equilibrium dissociation constant (e.g., a Skatchard plot). This set-up could also be used to analyze a sample fluid and measure biomolecular binding kinetics. This embodiment of the system 100 is a marked improvement over conventional methods which require performing many experiments in serial or parallel with physically separated sensors, multiple fluid handling components, and/or separately prepared concentrations.

It should be noted that in the past there have been described different methods for generating concentration gradients in a sample located in a microfluidic device. Several of the methods are disclosed in the following documents the contents of which are incorporated herein by reference:

U.S. Pat. No. 5,869,004 entitled "Methods and Apparatus for In Situ Concentration and/or Dilution of Materials in Microfluidic Systems".

Dertinger, S. K. W. et al. "Generation of Gradients having Complex Shapes using Microfluidic Networks. Anal. Chem. 2001, vol. 73, pp. 1240-1246.

U.S. Patent Application No. 2002/0113095 A1 entitled "Method and Apparatus for Gradient Generation".

Any of these methods for generating concentration gradients in a sample located in a microfluidic device can be implemented in this embodiment of the present invention.

Figure 12A:
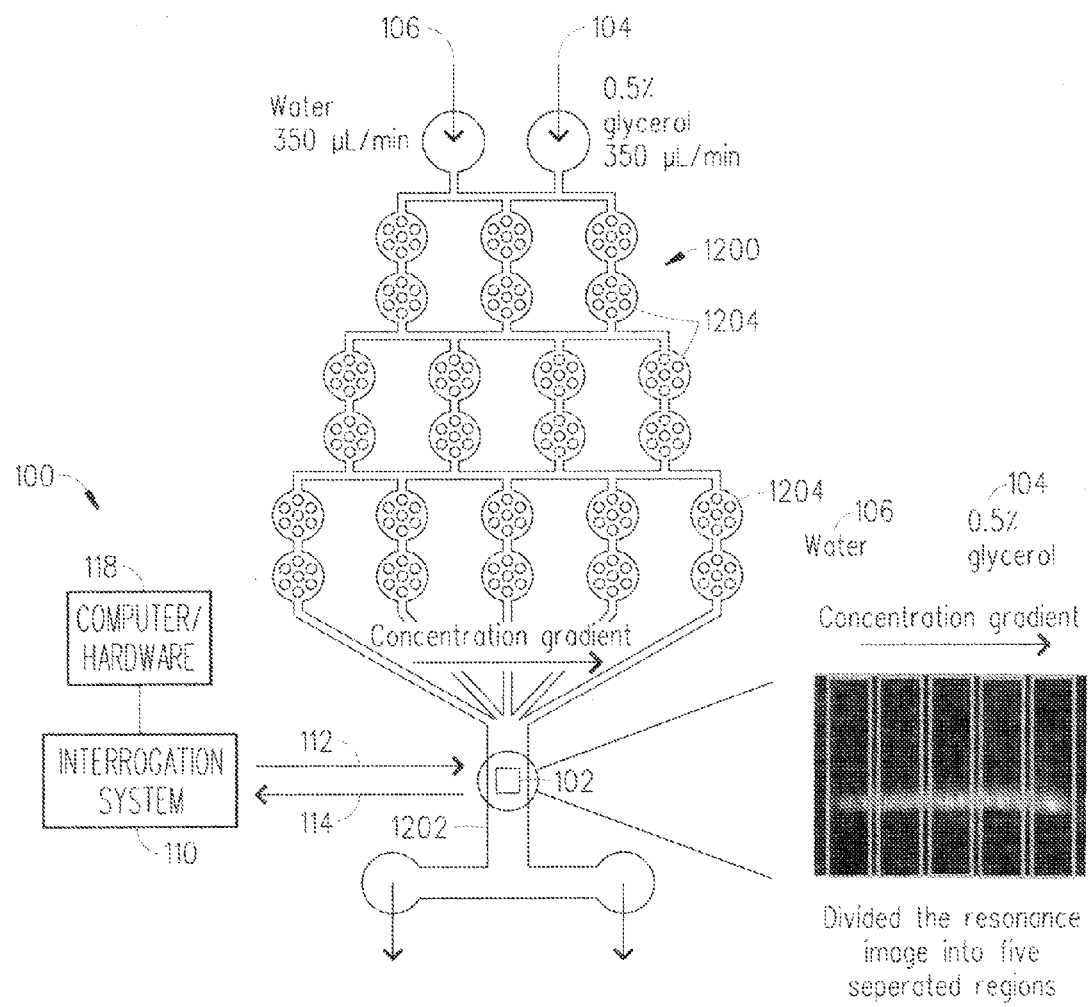
FIGS. 12A-12C illustrate several diagrams of a fourth embodiment of the system shown in FIG. 1 which analyzes a microfluidic device that is capable of generating multiple concentration gradients in a sample solution in accordance with the present invention.
Figure 12B:
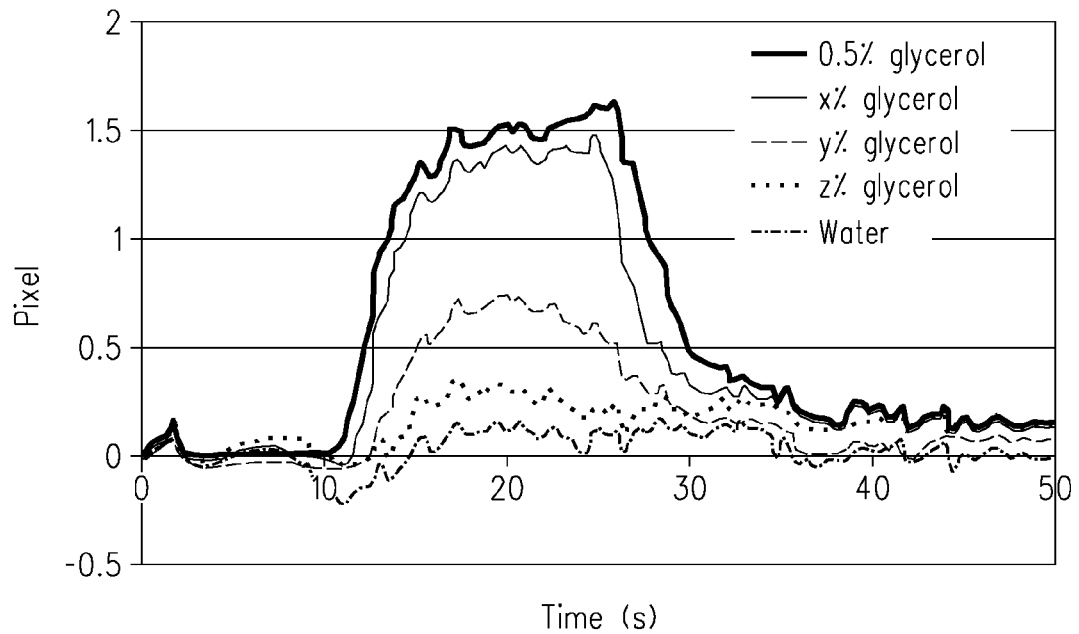
Figure 12C:
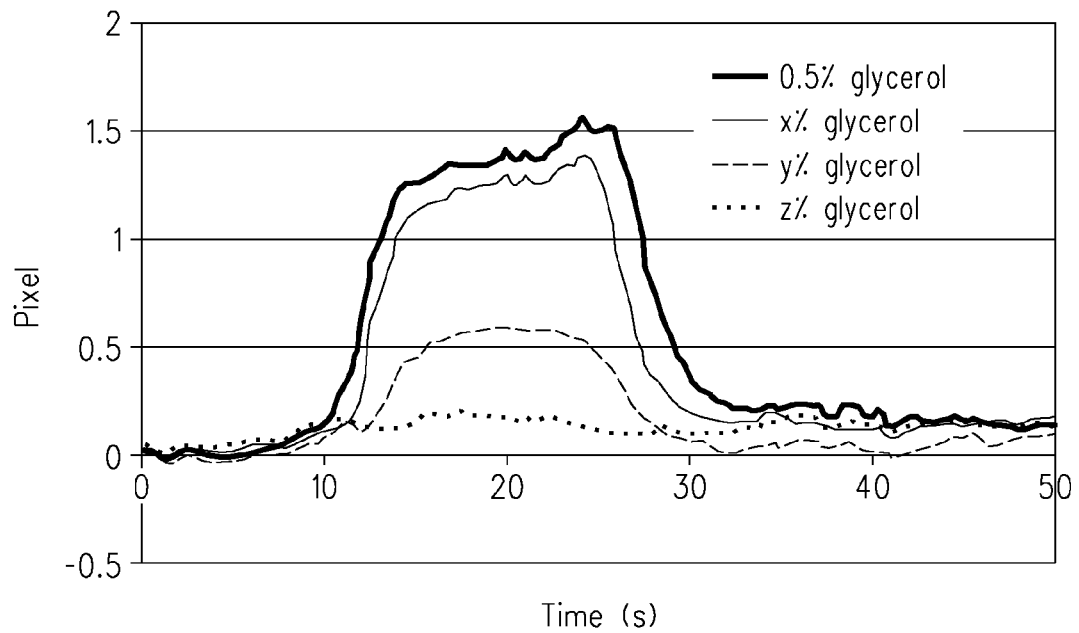

FIGS. 12A-12C illustrate several diagrams of a fourth embodiment of the system 100. In this embodiment, the interrogation system 110 outputs the optical beam 112 to the sensor 102 and receives the optical response 114 from across the sensor 102 which is then divided by the computer 118 into independent signals corresponding to each concentration of the sample fluid 104 and the reference fluid 106 in the flow chamber 1202. In particular, the microfluidic device/mixer 1200 generates multiple concentration gradients in the sample solution 104 which flows in a micron-sized deep flow chamber 1202. And, the computer 118 analyzes the output optical beam 114 to determine multiple corrected detection signals 124 which correspond with the multiple concentration gradients in the sample solution 104.

FIGS. 12A-12C are a series of figures that show how one embodiment of the present invention can enable multiplexing detection using a surface sensor 102. In a demonstration experiment, the two incoming fluid samples of water 106 and a 0.5 glycerol solution 104 were divided successively by mixers 1204 into three, four and five streams with each stream corresponding to a different concentration of the glycerol solution 104 (see FIG. 12A). After combining the streams into a single, micron-deep wide channel 1202, a gradient of glycerol solution concentration 104 was formed across the micron-deep channel 1202, perpendicular to the direction of flow (see FIG. 12A). The micron-deep wide channel 1202 was superimposed on top of a 3 mm×3 mm waveguide grating surface sensor 102. The optical detection system 100 with a CCD camera 412 shown in FIG. 4 was used to obtain an image of the sensor response which was divided into five regions to produce five separate angular resonance plots (see photo in FIG. 12A). Since the streams flowed across the same sensor 102 without mixing, the single sensor 102 provided a response to each flow stream independently and the five "zones" of the sensor exhibited response only to the local fluid above each zone (see photo in FIG. 12A). Also, the subtracted or referenced traces shown in the graphs of FIGS. 12B and 12C indicates that measurement noise and drift were significantly diminished, leading to smoother (less noisy) response.

From the foregoing, it can be readily appreciated by those skilled in the art that the present invention enables a simple and highly flexible self-referencing method for sensors within micron-depth flow chambers. Unlike the prior art, only one sensor is required for both simultaneous detection and referencing, which reduces the complexity of the optics and the instruments. The reference signal is generated from the same sensor used for the detection. Thus, the reference signal experiences the same environmental fluctuations as the detection signal. This increases the accuracy of the referencing and reduces uncertainty due to environmental conditions. Using the preferred embodiment of the system 100 shown in FIG. 4, the referencing area can be interrogated within the flow chamber without adding any additional sensors and the active sensor region can be adjusted via software to avoid the addition of new sensors and detection optics. Furthermore, unlike the prior art, the fluidic interface between detection and reference fluids is kept constant, preventing turbulent mixing, hysteresis, and repeatability problems inherent in moving fluidic interface systems.

It should be noted that the preferred sensors 102 used in the present invention are grating-coupled waveguide sensors 102 or surface plasmon resonance sensors 102. The following documents disclose details about the structure and the functionality of exemplary sensors 102 that can be used in the present invention:

European Patent Application No. 0 202 021 A2 entitled "Optical Assay: Method and Apparatus".

U.S. Pat. No. 4,815,843 entitled "Optical Sensor for Selective Detection of Substances and/or for the Detection of Refractive Index Changes in Gaseous, Liquid, Solid and Porous Samples".

The contents of these documents are incorporated be reference herein.

It should also be noted that for clarity the system 100 shown in FIGS. 1, 4, 7 and 11 is illustrated as having only one optical beam which interfaces with one sensor 102. Of course, the system 100 can have the hardware (e.g., optics, multiplexed optical detectors 414, spectrograph 714, CCD camera 412) that make it possible to emit and receive multiple optical beams to and from multiple sensors 102. The multiple sensors 102 can be incorporated in a multiple sensor plate.

Although multiple embodiments of the present invention have been illustrated in the accompanying Drawings and described in the foregoing Detailed Description, it should be understood that the invention is not limited to the embodiments disclosed, but is capable of numerous rearrangements, modifications and substitutions without departing from the spirit of the invention as set forth and defined by the following claims.

What is claimed is:

1. A system comprising:
    a sensor;
    a micron-sized deep flow channel in which a sample solution and a reference solution flow side-by-side to one another in a single sensing region of said sensor, wherein the single sensing region is divided into a detection region and a reference region which are contiguous to one another and which are respectively interfaced with the sample solution and the reference solution that flow side-by-side to one another in a longitudinal direction within the micron-sized deep flow channel;
    an interrogation system configured to direct an input optical beam at said sensor and receiving an output optical beam from said sensor;
    said interrogation system including a camera configured to convert the output optical beam to an electrical signal representative of an output image;
    a computer configured to analyze the output image to determine a detection signal associated with the sample solution flowing in the detection region of said sensor and to determine a reference signal associated with the reference solution flowing in the reference region of said sensor; and
    said computer configured to subtract the reference signal from the detection signal to generate a corrected detection signal, wherein uncertainties in the detection signal due to environmental conditions are reduced in the corrected detection signal.

2. The system of claim 1, wherein said corrected detection signal indicates whether or not a biomolecular binding event occurred in the sample solution flowing in said micron-sized deep flow channel.

3. The system of claim 1, wherein said sensor is a grating-coupled waveguide sensor or a surface plasmon resonance sensor.

4. The system of claim 1, wherein said micron-sized deep flow channel and said sensor are incorporated within a H-well plate.

5. The system of claim 1, wherein said interrogation system is an angular interrogation system in which the input optical beam has a single wavelength and is delivered to said sensor and in which the output optical beam is received from said sensor at the camera which is an optical detector or a charge-coupled device camera.

6. The system of claim 1, wherein said interrogation system is a spectral interrogation system in which the input optical beam is a collimated optical beam containing a plurality of wavelengths and is delivered to said sensor and in which the output optical beam is received from said sensor at the camera which is a spectrograph.

7. The system of claim 1, wherein said micron-sized deep flow channel is configured to receive a plurality of concentration gradients in the sample solution at the same time and said computer is configured to analyze the output optical beam to determine a plurality of detection signals corresponding to said plurality of concentration gradients in the sample solution.

8. A system comprising:
    a sensor;
    a micron-sized deep flow channel in which a sample solution and a reference solution flow side-by-side to one another in a single sensing region of said sensor, wherein the single sensing region is divided into a detection region and a reference region which are contiguous to one another and which are respectively interfaced with the sample solution and the reference solution that flow side-by-side to one another in a longitudinal direction within the micron-sized deep flow channel;
    an interrogation system configured to direct an input optical beam at said sensor and receiving an output optical beam from said sensor;
    said interrogation system including an optical detector configured to convert the output optical beam to separate electrical signals, one each representing a detection signal associated with the sample solution flowing in the detection region of said sensor and another representing a reference signal associated with the reference solution flowing in the reference region of said sensor; and
    a computer/electrical circuit configured to subtract the reference signal from the detection signal to generate a corrected detection signal, wherein uncertainties in the detection signal due to environmental conditions are reduced in the corrected detection signal.

9. The system of claim 8, wherein said corrected detection signal indicates whether or not a biomolecular binding event occurred in the sample solution flowing in said micron-sized deep flow channel.

10. The system of claim 8, wherein said sensor is a grating-coupled waveguide sensor or a surface plasmon resonance sensor.

11. The system of claim 8, wherein said micron-sized deep flow channel and said sensor are incorporated within a H-well plate.

12. The system of claim 8, said interrogation system is an angular interrogation system in which the input optical beam has a single wavelength and is delivered to said sensor and in which the output optical beam is received from said sensor at the camera which is an optical detector or a charge-coupled device camera.

13. The system of claim 8, wherein said interrogation system is a spectral interrogation system in which the input optical beam is a collimated optical beam containing a plurality of wavelengths and is delivered to said sensor and in which the output optical beam is received from said sensor at the camera which is a spectrograph.

14. The system of claim 8, wherein said micron-sized deep flow channel is configured to receive a plurality of concentration gradients in the sample solution at the same time and said computer/electrical circuit is configured to analyze the output optical beam to determine a plurality of detection signals corresponding to said plurality of concentration gradients in the sample solution.

* * * * *